| United States Patent [19] | [11] | 4,115,436 |
|---|---|---|
| Katsuragawa et al. | [45] | * Sep. 19, 1978 |

[54] PROCESS FOR PRODUCING AMMONIUM P-STYRENESULFONATE

[75] Inventors: Kanzi Katsuragawa; Tatsuo Hattori; Keiichi Kihara; Hanzo Tamabayashi, all of Shin-nanyo, Japan

[73] Assignee: Toyo Soda Manufacturing Co., Ltd., Japan

[*] Notice: The portion of the term of this patent subsequent to Dec. 6, 1994, has been disclaimed.

[21] Appl. No.: 813,846

[22] Filed: Jul. 8, 1977

Related U.S. Application Data

[63] Continuation of Ser. No. 608,701, Aug. 28, 1975, Pat. No. 4,061,669.

[51] Int. Cl.$^2$ ............................................ C07C 143/24
[52] U.S. Cl. ................................................. 260/505 N
[58] Field of Search ............ 260/505 N, 505 R, 501.21

[56] References Cited

U.S. PATENT DOCUMENTS 2,451,549   10/1948   Gzemski ............................... 260/505

*Primary Examiner*—A. Siegel
*Attorney, Agent, or Firm*—Oblon, Fisher, Spivak, McClelland & Maier

[57] ABSTRACT

Ammonium p-styrenesulfonate is produced in a process which comprises reacting an amine having more than 7 carbon atoms and a mineral acid with an alkali metal p-styrenesulfonate in an aqueous media to produce an amine salt of p-styrenesulfonic acid and then reacting ammonia with said amine salt.

4 Claims, 1 Drawing Figure

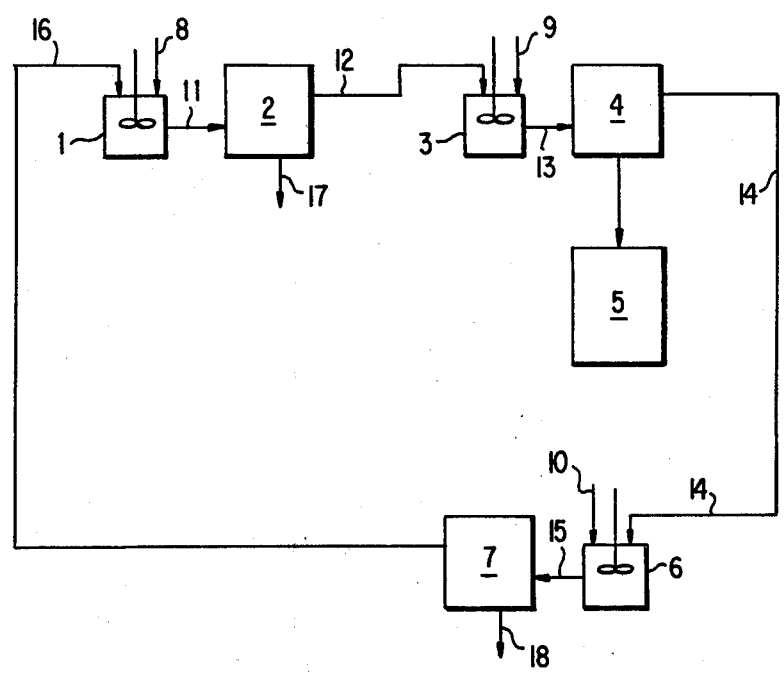

PROCESS FOR PRODUCING AMMONIUM P-STYRENESULFONATE

This is a continuation of application Ser. No. 608,701, filed Aug. 28, 1975 now U.S. Pat. No. 4,061,669.

BACKGROUND OF THE INVENTION

1. Field of the Invention

The present invention relates to a process for producing ammonium p-styrenesulfonate from an alkali metal p-styrenesulfonate.

2. Description of the Prior Art

Heretofore, it has been known that ammonium salts of organic sulfonic acids can be produced easily by neutralizing the corresponding sulfonic acids with ammonia. However, in the production of ammonium p-styrenesulfonate, the precursor p-styrenesulfonic acid is not easily produced by such conventional techniques as sulfonation of styrene or the like. Accordingly, it is difficult to utilize the usual methods. As shown in the disclosure of Japanese Patent Publication No. 14220/1960, it has been known that alkali metal p-styrenesulfonates can be produced by reacting an alkali hydroxide with β-haloethylbenzenesulfonic acid.

The inventors have previously attempted to produce ammonium p-styrenesulfonate from alkali metal p-styrenesulfonate, and have found that ammonium p-styrenesulfonate can be produced by reacting an inorganic ammonium salt with an alkali metal p-styrenesulfonate in an alcohol solvent or in a mixture of an organic solvent with water. However, it is very difficult to prevent the contamination of the product by a small amount of alkali metal component. Consequently, a need continues to exist for an effective process for preparation of ammonium p-styrenesulfonate in a non-contaminated form.

SUMMARY OF THE INVENTION

Accordingly, it is an object of the present invention to provide a process for producing in high conversion, ammonium p-styrenesulfonate which contains substantially no alkali metal component.

Briefly, this and other objects of this invention as will hereinafter become clear by the ensuing discussion, have been achieved by providing a process for producing ammonium p-styrenesulfonate which comprises reacting an amine having more than 7 carbon atoms and a mineral acid with an alkali metal (preferably Na or K) p-styrenesulfonate in a solvent of water or of a mixture of an organic solvent and water, to produce an amine salt of p-styrenesulfonic acid and then reacting ammonia with said amine salt.

Alternatively, this invention provides a continuous process for producing ammonium p-styrenesulfonate from an alkali metal (preferably Na or K) p-styrenesulfonate which comprises producing an amine salt of p-styrenesulfonic acid by contacting an aqueous solution of an alkali metal p-styrenesulfonate with a solution of a mineral acid salt of an organic amine having more than 7 carbon atoms in an organic solvent; contacting the organic solution of the resultant amine salt of p-styrenesulfonic acid with ammonia to produce ammonium p-styrenesulfonate and to recover the organic amine; and reacting the organic amine with a mineral acid to recover the mineral acid salt of the organic amine and recycling this salt back to the first step.

BRIEF DESCRIPTION OF THE DRAWINGS

A more complete appreciation of the invention and many of the attendant advantages thereof will be readily attained as the same becomes better understood by reference to the following detailed description when considered in connection with the accompaying drawing, wherein:

FIG. 1 contains a flow diagram of one embodiment of the continuous process of this invention.

DETAILED DESCRIPTION OF THE PREFERRED EMBODIMENTS

The process of this invention using the specific amines described above is based upon the following reactions.

The reaction of the amine and the mineral acid with alkali metal p-styrenesulfonate can be represented as follows:

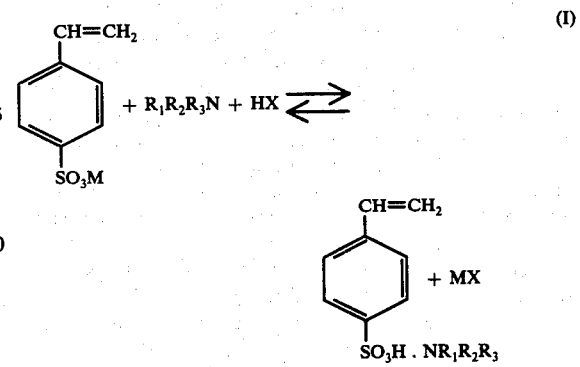

(1)

wherein M represents an alkali metal such as Na or K; HX represents a mineral acid such as HCl, $H_2SO_4$, HBr and the like; and $R_1$, $R_2$ and $R_3$ represent H or an alkyl or aryl group and at least one of $R_1$, $R_2$ and $R_3$ is such an alkyl or aryl group, and the number of carbon atoms in the amine is greater than 7. As shown below, there is no critical upper limit on the number of carbon atoms permissible. When reaction (1) is conducted in an aqueous solution, a water-insoluble amine salt of p-styrenesulfonic acid can be produced only by using an amine having many carbon atoms. Thereby, the equilibrium is shifted to the right-hand side of the equation so as to produce a water soluble alkali metal salt of the mineral acid and a water insoluble amine salt of p-styrenesulfonic acid.

The reaction of the amine salt of p-styrenesulfonate with ammonia water can be shown as follows:

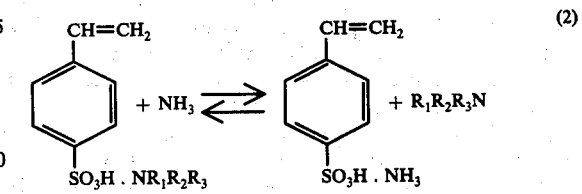

(2)

When reaction (2) is conducted in an aqueous solution, the equilibrium is shifted to the right-hand side of the equation to produce amine and an aqueous solution of ammonium p-styrenesulfonate.

Suitable amines having the formula $R_1R_2R_3N$ as shown in the reaction formulae (1) and (2) include primary amines, secondary amines and tertiary amines. The amines must have more than 7 carbon atoms, can be solids or liquids at room temperature and are insoluble or sparingly soluble in water. Suitable amines having more than 7 carbon atoms include primary amines such as 2-ethylhexylamine, octylamine, decylamine, laurylamine, coconut amine, myristylamine, oleylamine, coconutalkylamine, or the like; secondary amines such as di-2-ethylhexylamine and the like; tertiary amines such as tri-2-ethylhexylamine; dimethyloctylamine, dimethyldecylamine, dimethyllaurylamine, dimethylcoconut amine, dimethylmyristrylamine, hexadecyldimethylamine, methyldilaurylamine, dimethylstearylamine, tricaprylamine, coconutalkyldimethylamine and the like; aromatic primary amines such as toluidine, xylidine, trimethylaniline, ethylaniline, propylaniline, naphthylamine, and the like; aromatic secondary amines such as N-methyltoluidine, N-methylaniline, N-ethylaniline, diphenylamine, N-phenyltolylamine, ditolylamine and the like; aromatic tertiary amines such as N,N-dimethyltoluidine, N,N-diethylaniline, N-methyldiphenylamine and the like; and ion-exchange liquids having a molecular weight of 200 – 600 such as primary amines such as N-dodecenyl(tri $C_{12-15}$ alkylmethyl) amine, N-lauryl(tri $C_{12-15}$ alkylmethyl) amine and the like; secondary amines such as trialkylamines (total number of carbon atoms: 15-23) and the like; trialkylmethylamine (total carbon atoms 18-24) and the like; tris(tridecyl) amine and the like; and ion-exchange resins having functional groups of primary, secondary or tertiary amine groups, especially styrene polymers and formaline polymers having primary, secondary or tertiary amine groups, such as weak basic anion-exchange resins having functional groups of $-N(R)_2$, $-NH(R)$ and $-NH_2$; weak basic anion-exchange resins having functional groups of $-N(CH_3)_2$; basic anion-exchange resins having functional groups of $-N(R)_2$; weak basic anion-exchange resins of polyamine, and the like.

When the amine salt of p-styrenesulfonic acid and the amine are precipitated as solids in reaction (1), they can be separated from the alkali metal salt of the mineral acid by filtration. The ammonium p-styrenesulfonate produced in reaction (2) can be obtained as an aqueous solution by removing the amine by filtration. In the reaction (1), when the amine or the amine salt of p-styrenesulfonic acid is not precipitated as a solid, it is possible to separate the liquid phase of the insoluble amine or the water insoluble amine salt of p-styrenesulfonic acid from the aqueous solution. However, the amine and amine salt of p-styrenesulfonic acid are viscous liquids and accordingly, it is sometimes difficult to separate them as liquids. Consequently, the inventors have attempted to develop a technique to separate the amine from the aqueous solution or to separate the amine salt of p-styrenesulfonic acid from the aqueous solution using industrially applicable methods. As a result, it has been found that the amine and the amine salt of p-styrenesulfonic acid can be dissolved in certain organic solvents which are not miscible with water. These organic solvents include hydrocarbons having more than 5 carbon atoms, monohydric alcohols having more than 4 carbon atoms, esters having more than 4 carbon atoms, ketones having more than 4 carbon atoms and ethers having more than 4 carbon atoms. The particular solvent to be used can be selected according to conventional considerations regarding extraction processes. When these organic solvents are used, ammonium p-styrenesulfonate can be effectively produced by an extracting operation regardless of whether the amine and the amine salt of p-styrenesulfonic acid are in the solid or liquid form. In either case, they can be easily separated from the aqueous solution. Moreover, both the contamination of the aqueous solution of ammonium p-styrenesulfonate by the amine and the loss of the amine to be used for recycling can be advantageously prevented.

When the organic solvent is not used, the amine and the mineral acid are first mixed to produce the amine salt of the mineral acid. This can then be added to an alkali metal p-styrenesulfonate to produce the amine salt of p-styrenesulfonic acid. When the organic solvent is used, it is also possible to produce the amine salt of p-styrenesulfonic acid by treating an aqueous solution of the alkali metal p-styrenesulfonate with the amine salt of the mineral acid which has been previously produced. When the ion-exchange resin is used, the functional groups are converted to $X^-$ type and then an aqueous solution of an alkali metal p-styrenesulfonate is added to the ion-exchange resin. Alternatively, an equivalent amount of the mineral acid and an alkali metal p-styrenesulfonate are added to the ion-exchange resin to produce the amine salt of p-styrenesulfonic acid and then ammonia water is added to produce the ammonium p-styrenesulfonate.

The continuous process for producing ammonium p-styrenesulfonate from an alkali metal p-styrenesulfonate will be illustrated by reference to the figure, in which a three mixer-settler type counter-flow extraction apparatus is employed. In an extractor 1, a solution of an amine salt of a mineral acid in an organic solvent 16 is contacted with an aqueous solution of an alkali metal styrenesulfonate 8. In a settler 2, the reaction mixture 11 fed from the extractor 1 is separated into a water phase and an organic phase. The water phase 17 is fed to a suitable treating apparatus for waste. In an extractor 3, the organic phase 12 fed from the settler 2 is contacted with ammonia water 9. In a settler 4 the reaction mixture 13 fed from the extractor 3 is separated into a water phase and an organic phase. The water phase is fed to a product tank 5 and, if desirable, is concentrated and ammonia is removed. In an extractor 6, the organic phase 14 fed from the settler 4 is contacted with an aqueous solution of mineral acid 10. In a settler 7, the reaction mixture 15 fed from the extractor 6 is separated into a water phase and an organic phase. The water phase 18 is fed to a suitable treating apparatus for waste or is treated to recover the mineral acid. The organic phase containing the amine salt of mineral acid 16 is recovered and recycled. In the continuous process, the amount of the amine relative to the organic solvent is preferably in the range of 5 – 40 wt%. The concentration of the aqueous solution of the alkali metal styrenesulfonate should be in the range of from 1 wt% to a saturated concentration. Neither of these concentrations are critical. The mineral acids are preferably hydrochloric acid, sulfuric acid, hydrobromic acid or anhydrides thereof. When ammonium styrenesulfonate having especially high purity is desired, the amount of the amine salt of mineral acid should be less than the equivalent amount relative to the alkali metal p-styrenesulfonate. When loss of the alkali metal p-styrenesulfonate must be prevented, multi-stage extractions should be conducted. When excess of the amine salt of mineral acid is used, the loss of the alkali metal p-styrenesulfonate is small even in a one-stage extraction. However, the product can be contaminated with the ammonium salt of the mineral acid. In the second extraction step for extracting styrenesulfonic acid anion with ammonia water, the amount of ammonia should be more than the equivalent amount relative to the amine salt of the mineral acid in order to increase the extraction coefficient.

The process of the invention has the following advantages:

(1) In the reaction for producing the amine salt of p-styrenesulfonate, all of the alkali metal salts are water soluble and can be completely separated from the water insoluble amine salt of p-styrenesulfonate. Accordingly, the ammonium p-styrenesulfonate product does not contain an alkali metal salt impurity.

(2) Even though water soluble impurities may be contained in the starting material of alkali metal p-styrenesulfonate, the impurities can be separated from the amine salt of p-styrenesulfonic acid. Accordingly, the purity of the ammonium p-styrenesulfonate product is not decreased.

(3) The amine can be repeatedly used for the production of ammonium p-styrenesulfonate by recycling.

Having generally described the invention, a more complete understanding can be obtained by reference to certain specific examples, which are included for purposes of illustration only and are not intended to be limiting unless otherwise specified.

EXAMPLE 1

A 20.6 g sample of sodium p-styrenesulfonate was dissolved in 100 g of water. 14.4 g of p-toluidine hydrochloride was added to the resulting solution to precipitate a solid. The solid was filtered and was dissolved in 100 cc of aqueous solution containing 20 cc of 28.8% $NH_3$ solution. As a result, ammonium p-styrenesulfonate was obtained in a conversion of 76%.

EXAMPLE 2

The salt of p-styrenesulfonate was extracted from an aqueous solution of 20.6 g of sodium p-styrenesulfonate in 200 g of water with a solution of 14.4 g of p-toluidine hydrochloride in 200 g of n-butanol. It was further extracted with 300 cc of an aqueous solution containing 20 cc of 28.8% $NH_3$ solution. As a result, ammonium p-styrenesulfonate was obtained in a conversion of 78%. The product contained 12% of unreacted sodium p-styrenesulfonate.

EXAMPLE 3

The salt of p-styrenesulfonate was extracted from an aqueous solution of 10.3 g of sodium p-styrenesulfonate in 100 g of water with a solution of 6.8 g of p-toluidine hydrochloride in 200 g of n-amylalcohol. It was further extracted with 200 cc of an aqueous solution containing 20 cc of 28.8% $NH_3$ solution. As a result, ammonium p-styrenesulfonate was obtained in a conversion of 95%. The product did not contain unreacted sodium p-styrenesulfonate.

EXAMPLES 4–6

130 cc of each ion-exchange liquid listed in Table 1 were dissolved in ligroin and 300 cc of 1N—HCl was added to each solution to produce an ion-exchange solution hydrochloride. The salt of p-styrenesulfonate was extracted from an aqueous solution of 50 g of sodium p-styrenesulfonate in 280 g of water with said solution and was further extracted with 300 cc of 4% $NH_3$ aqueous solution. As a result, ammonium p-styrenesulfonate was obtained in the conversions shown in Table 1.

TABLE 1

| Example No. | Ion-Exchange liquid (%) | Concentration of ion-exchange liquid (%) | Conversion to ammonium p-styrenesulfonate (%) |
|---|---|---|---|
| 4 | LA - 1 | 15.8 | 93.6 |
| 5 | LA - 1 | 28.9 | 86.6 |
| 6 | LA - 2 | 21.0 | 94.7 |

Note:
LA - 1 N-dodecenyl (tri $C_{12-15}$ alkylmethyl) amine.
LA - 2: N-lauryl (tri $C_{12-15}$ alkylmethyl) amine.

EXAMPLE 7

A 350 cc sample of an ion-exchange liquid (LA-2) was dissolved in 1300 cc of ligroin, and 1 liter of 1N—HCl was added to the liquid to produce an ion-exchange liquid hydrochloride. The salt of p-styrenesulfonate was extracted from an aqueous solution of 180 g of sodium p-styrenesulfonate in 1 liter of water with said solution. It was further extracted from the extracted solution with 1.2 liters of 4% $NH_3$ aqueous solution, repeatedly. As a result, ammonium p-styrenesulfonate was obtained without decrease of extraction efficiency of the extracting solution in the following conversions.

| Repeated Extractions (times) | Conversion to ammonium p-styrenesulfonate (%) |
|---|---|
| 1 | 94.0 |
| 2 | 95.9 |
| 3 | 95.8 |
| 4 | 93.5 |
| 5 | 94.7 |
| 6 | 93.9 |
| 7 | 93.7 |

EXAMPLE 8

A 500 ml portion of ion-exchange resin (IR-45) (weak basic anion exchange resin having the functional groups of —N(R)$_2$, —NH(R), —NH$_2$, a density of 670 g/l, an effective diameter of 0.36 - 0.46 μm, a total exchange capacity of 5.2 mg equivalent/ml dry) was treated with 2.5 liter of 0.5 N HCl solution to convert it to the Cl salt and the ion-exchange resin was washed with 3 liters of water. An aqueous solution of 180 g of sodium p-styrenesulfonate in 3 liters of water was passed through a column filled with the ion-exchange resin in two hours, and the ion-exchange resin was washed with 3 liters of water. A 3 liter aqueous solution of 200 ml of 28.8% $NH_3$ aqueous solution was passed through the ion-exchange resin. As a result, ammonium p-styrenesulfonate was obtained in a conversion of 84.5%.

EXAMPLE 9

A 300 ml portion of ion-exchange resin (IRA-93) (weak-basic anion-exchange resin having functional groups of —N(CH$_3$)$_2$, a density of 610 g/l, an effective diameter of 0.40 - 0.50 μm, a total exchange capacity of 4.8 mg equivalent/ml dry) was filled into a chromatographic column and was treated with 1.5 liters of 0.5N HCl solution to convert it to the Cl salt and the ion-exchange resin was washed with 3 liters of water. An aqueous solution of 80 g of sodium p-styrenesulfonate in 1 liter of water was passed through the column filled with the ion-exchange resin in 2 hours and the ion-exchange resin was washed with 3 liters of water. A 3 liter aqueous solution of 100 ml of 28.8% NH₃ aqueous solution was passed through the ion-exchange resin. As a result, ammonium p-styrenesulfonate was obtained in a conversion of 89.5%.

EXAMPLE 10

A mixer-settler type counter-flow extraction apparatus comprising a 0.5 liter extractor equipped with a stirrer and a 1.5 liter settler was used. An aqueous solution of 15.0 wt% of sodium styrenesulfonate was fed at a rate of 14.8 g/min. An extraction reagent of 20 wt% of an ion-exchange liquid (LA-2) of N-lauryl (tri $C_{12-15}$ alkylmethyl)amine hydrochloride in n-heptane was fed at a rate of 20.6 g/min (about 0.010 mole/min as $Cl^-$) so as to conduct a continuous extraction by simultaneous feeding. The upper n-heptane phase separated in the settler was fed to the same type mixer-settler type counter-flow extraction apparatus and a 1.8 wt% NH₃ aqueous solution was simultaneously fed at a rate of 10.7 g/min. Thereby, styrenesulfonic acid anion was continuously counter-extracted into the water phase as ammonium styrenesulfonate. The water phase solution was stored in a tank. 4.20 kg of the resulting solution was concentrated at 50° C under 90 mm Hg to 3.51 kg. According to an analysis, the following components were found.

| | |
|---|---|
| $CH_2=CH-\langle\bigcirc\rangle-SO_3^-$ | 17.6 wt % |
| $Na^+$ | 0.03 wt % |
| $NH_4^+$ | 1.78 wt % |
| $Cl^-$ | 0.01 wt % |

The solution of LA-2 in n-heptane left after the counter-extraction as the upper phase, was contacted with a 10% HCl aqueous solution fed at a rate of 4.1 g/min in the same type counter-flow extraction apparatus so as to recover as a solution about 20 wt% of the LA-2 hydrochloride in n-heptane.

EXAMPLE 11

In accordance with the process of Example 10, in the counter-flow extraction apparatus of Example 1, an aqueous solution of 15 wt % potassium styrenesulfonate was fed at a rate of 20.5 g/min instead of the solution of sodium styrenesulfonate. A solution of 20 wt% of trialkylmethylamine (total carbon atoms: 18 – 24) hydrochloride in n-octyl alcohol was fed at a rate of 22.4 g/min (0.013 mole/min as $Cl^-$) instead of the solution of La-2 hydrochloride in n-heptane and a 1.8 wt% NH₃ aqueous solution was fed at a rate of 13.6 g/min. 4.83 kg of the resulting solution was concentrated at 50° C under 90 mm Hg to 3.66 kg. According to an analysis, the following components were found.

| | |
|---|---|
| $CH_2=CH-\langle\bigcirc\rangle-SO_3^-$ | 19.6 wt % |
| $K^+$ | 0.06 wt % |
| $NH^+$ | 1.95 wt % |
| $Cl^-$ | 0.01 wt % |

The solution of trialkylmethylamine in n-octyl alcohol left after the counter-extraction was treated with a 10% HCl aqueous solution in accordance with the process of Example 10.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for producing ammonium p-styrenesulfonate which comprises reacting an amine having more than 7 carbon atoms and less than 600 MW, and a mineral acid or a mineral acid salt of an amine having more than 7 carbon atoms and less than 600 MW with an alkali metal p-styrenesulfonate in an aqueous or an aqueous organic solvent to produce an amine salt of p-styrenesulfonic acid as a precipitate in said aqueous solvent or a solution in said aqueous organic solvent and then reacting ammonia with said amine salt as the precipitate or the solution.

2. The process of claim 1, wherein said solvent is water.

3. The process of claim 1, wherein said solvent is a mixture of an organic solvent and water.

4. A process for producing ammonium p-styrenesulfonate which comprises reacting a solution of p-toluidine hydrochloride in n-amylalcohol with an aqueous solution of sodium p-styrenesulfonate to produce the toluidine salt of p-styrenesulfonic acid and then reacting ammonia with said salt.

* * * * *